United States Patent [19]

Saito et al.

[11] Patent Number: 4,798,704
[45] Date of Patent: Jan. 17, 1989

[54] PREHEATING APPARATUS EMPLOYED IN ANALYSIS OF HYDROGEN AND CARBON

[75] Inventors: Keiji Saito, Okayama; Yoshiro Takizawa, Chiba; Isao Takagi, Okayama, all of Japan

[73] Assignee: Kawasaki Steel Techno-Research Corporation, Tokyo, Japan

[21] Appl. No.: 915,554

[22] Filed: Oct. 6, 1986

[30] Foreign Application Priority Data

Oct. 7, 1985 [JP] Japan .................................. 60-223276

[51] Int. Cl.⁴ .......................................... G01N 33/20
[52] U.S. Cl. ...................................... 422/99; 422/68; 422/78; 436/144; 219/347
[58] Field of Search ...................... 422/99, 68, 78; 436/144; 219/347

[56] References Cited

U.S. PATENT DOCUMENTS 4,170,455 10/1979 Henrie .................................. 436/144

FOREIGN PATENT DOCUMENTS 53-12393 2/1978 Japan .

Primary Examiner—Benoit Castel
Assistant Examiner—Jill Johnston
Attorney, Agent, or Firm—Young & Thompson

[57] ABSTRACT

A preheating apparatus of an analysis apparatus for determining the in quantity hydrogen and carbon contained in a sample such as steel is employed to remove moisture adhered to a sample of the steel by spot-heating focused on the sample in a transparent bent tube which is turned one-half in its circumferential direction after completion of its preheating to make it possible for the sample to be transfered by gravity from the bent tube into a graphite crucible in which the sample is fused to extract hydrogen and carbon contained in the sample, so that the thus extracted hydrogen and carbon are determined.

4 Claims, 2 Drawing Sheets

PREHEATING APPARATUS EMPLOYED IN ANALYSIS OF HYDROGEN AND CARBON

BACKGROUND OF THE INVENTION

1. Field of the Invention

The present invention relates to a preheating apparatus employed in analysis of hydrogen and carbon contained in a sample, and more particularly to an improvement of such preheating apparatus for previously removing moisture and carbon both of which are adhering to a steel sample to make it possible to conduct analysis of hydrogen and carbon of the sample.

In the preheating apparatus of the present invention, it is possible to preheat various metals and alloys thereof as the samples for analysis of hydrogen and carbon. Of the metals and alloys thereof, steel will be hereinbelow described in detail, for convenience' sake, as a typical one of the samples.

2. Description of the Prior Art

Hitherto, as a hydrogen analysis method for the steel sample, there have been employed a hot-extraction method and an impulse furnace fusion-thermal conductivity method. In the hot-extraction method, the sample is heated in a quartz tube so that the crystal lattice of the sample is expanded to extract hydrogen. In this method, however, since the steel sample is heated to an excessively high temperature, moisture adhered to the steel sample is decomposed so that hydrogen is produced. Due to the thus produced hydrogen, there is a tendency for the determined value of hydrogen to be too high in such a hot-extraction method.

In contrast with the hot-extraction method, the impulse furnace fusion-thermal conductivity method requires not much time in its practical use (at most, only 5 minutes are required). In this method, however, in case that there is moisture adhered to the sample, the determined value of hydrogen become excessively large since the adhered moisture reacts on a graphite crucible to produce hydrogen by the water-gas reaction. In order to overcome such disadvantage, a preheating apparatus has been proposed. The preheating apparatus is employed to preheat the sample so that the moisture adhered to the sample is removed to prevent hydrogen from being produced by the water-gas reaction, whereby it is possible to obtain an accurately determined value of hydrogen in the analysis.

However, in the conventional preheating apparatus, a cooling system such as a water-jacket and the like is required due to employment of a tubular furnace provided with nichrome wire and the like. In addition, in the conventional preheating apparatus, the sample is held in a carrier gas and heated therein, and then transferred to a fusion furnace, so that such a complex handling operation is inherently bound to lead to many troubles in sealing of a joint section between the preheating apparatus and a main body of a hydrogen analysis apparatus, in addition to troubles in holding and transferring of the sample.

SUMMARY OF THE INVENTION

It is an object of the present invention to resolve the above problems so that there is provided a preheating apparatus employed in analysis of hydrogen and carbon both contained in steel, in which preheating apparatus is employed a heat-ray spot irradiating type heater for directly heating a sample in a transparent tube from outside, which transparent tube is rotatably driven to make it easy to transfer the sample that has been heated.

The above object of the present invention is accomplished by providing a preheating apparatus for removing mainly moisture and carbon both adhered to a sample before said sample is put into a furnace in which said sample is fused or heated to extract hydrogen and carbon in gaseous forms for conducting analysis of said hydrogen and carbon thus extracted, comprising:

a bent tube provided with a bent bottom portion in which said sample may be disposed;

a light source;

a focusing means for focusing a light issued from said light source on said bent bottom portion of said bent tube; and means for turning said bent tube one-half turn in a circumferential direction of said bent tube;

whereby said sample in said bent bottom portion of said bent tube is transferred from said bent bottom portion of said bent tube when said bent tube is rotatably driven.

BRIEF DESCRIPTION OF THE DRAWINGS

Hereinbelow, a preferred embodiment of the preheating apparatus of the present invention will be described in detail with reference to the drawings in which.

DESCRIPTION OF THE PREFERRED EMBODIMENT

Figure 1:
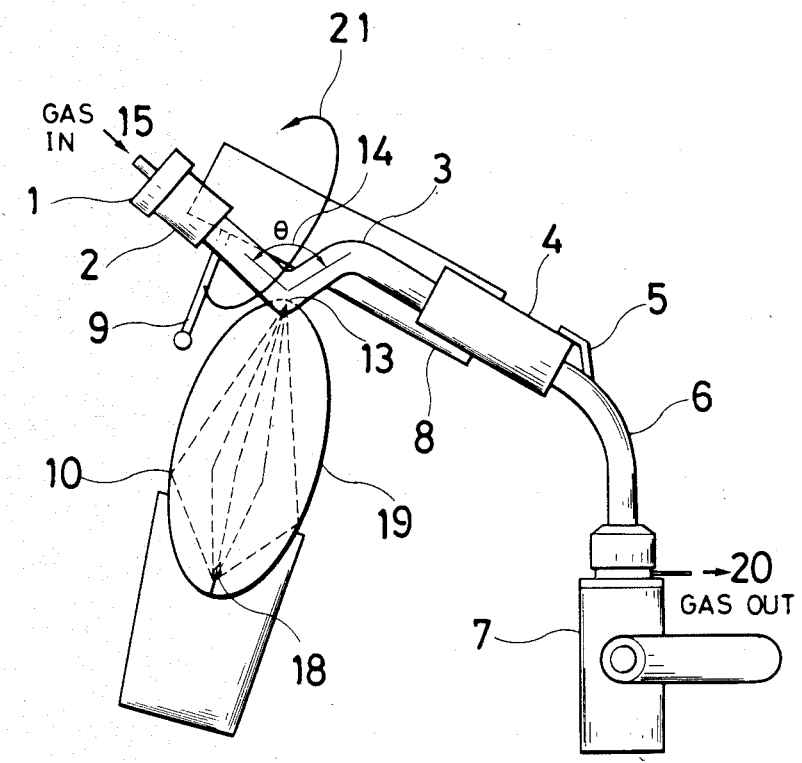
FIG. 1 is a side view of an embodiment of the preheating apparatus of the present invention.

The reference numeral 1 denotes a sample inlet sealing plug; 2 a sample inlet portion coupler; 3 a bent heating tube; 4 a lower coupler; 5 a coupler holding metal piece; 6 a stainless steel tube; 7 a ball valve; 8 a rotary plate; 9 a handle; 10 a heat-ray spot-irradiating type heater; 11 an O-ring holding metal piece; 12 an O-ring; 13 a bent bottom portion; 14 a bend angle $\theta$; 15 a carrier gas inlet; 16 an inner bore of the lower coupler; 17 a pair of O-rings; 18 an infrared lamp; 19 a concave mirror; 20 a carrier gas outlet; and 21 a direction of rotation.

As shown in FIG. 1, the preheating apparatus of the present invention is provided with a bent heating tube 3 having a transparent bent bottom portion 13 in which a steel sample may be disposed. An end portion of the bent heating tube 3 is connected to a sample inlet portion coupler 2 of a hydrogen analysis apparatus for analyzing gaseous hydrogen extracted from a steel sample having been fused in a fusion furnace. The other end portion of the bent heating tube 3 is connected with a stainless steel tube 6 which is hermetically connected to an impulse furnace (not shown) of a main body of the hydrogen analysis apparatus through the lower coupler 4.

A hydrogen analysis of the steel sample is so conducted that hydrogen is extracted from the steel sample, transferred with a carrier gas and measured, so that it is necessary to sufficiently seal the joint sections of the bent heating tube 3 with respect to both the sample inlet portion coupler 2 and the lower portion coupler 4 through the O-rings 12 and 17, respectively.

The preheating apparatus of the present invention is characterized by a shape of the bent heating tube 3 which may take any shape permitting the steel sample to reside therein and to be transferred therefrom when the bent heating tube 3 is rotatably driven. In the embodiment of the present invention shown in FIG. 1, the bent heating tube 3, which is obliquely disposed between the sample inlet coupler 2 and the lower coupler 4, is provided with a bent bottom portion 13 in which the steel sample charged from the sample inlet portion coupler 2 may be disposed. A bend angle $\theta$ of the bent heating tube 3 around the bent bottom portion 13 is in a range of 40° to 150°, preferably, in a range of 70° to 120°. When the angle $\theta$ is larger than 150°, the steel sample cannot be remain in the bent bottom portion 13 of the bent heating tube 3. When the angle $\theta$ is less than 40°, it is difficult to transport the steel sample by gravity when the bent heating tube 3 is rotatably driven so as to discharge the steel sample.

Since the bent heating tube 3 is heated to a temperature of 200° to 500° C., it is necessary that the bent heating tube 3 is transparent to infrared rays, also good in heat resistance and good in ease of treatment, so that it is preferable that the bent heating tube 3 is made of glass or quartz.

The preheating apparatus of the present invention is further characterized in that the preheating apparatus of the present invention is provided with means for easily rotatably driving the bent heating tube 3. This means for rotation is comprised by a handle 9 fixed to the rotary plate 8 to which are fixed the sample inlet coupler 2, the bent heating tube 3 and the lower coupler 4 as shown in FIG. 1. The means for rotation such as the handle 9 may take any form permitting the bent heating tube 3 to be turned one-half turn in its circumferential direction so that the steel sample, which is in the bent bottom portion 13 of the bent heating tube 3 and preheated, falls by gravity from the bent heating tube 3.

During rotary motion of the bent heating tube 3, in order to prevent the lower coupler 4 from being separated from the stainless steel tube 6, a coupler holding metal piece 5 is fixed to the stainless steel tube 6 so as to slide on an outer periphery of the lower coupler 4 during rotary motion of the bent heating tube 3.

When the handle 9 is manually rotated in a direction 21 of rotation by the operator, the rotary plate 8 is rotated in the same direction as the handle 9, so that all of the sample inlet coupler 2, bent heating tube 3 and the lower coupler 4 are rotated in the same direction as the rotary plate 8, whereby the steel sample in the bent bottom portion 13 falls by gravity through the stainless steel tube 6 when the bent bottom portion 13 of the bent heating tube 3 takes its highest position in rotation. In the preheating apparatus of the present invention, since it is possible to transfer the steel sample through such rotation, a stopper for discharging the sample is not required in contrast with the conventional tubular furnace from which the sample is discharged, to make it possible to increase the gas tightness of the joints of the preheating apparatus of the present invention by the use of O-rings.

In the preheating apparatus of the present invention, only the sample, which is at the bent bottom portion 13 of the bent heating tube 3, is heated by a heat-ray spot-irradiating type heater 10 in spot-heating manner. Although a light source for heating use takes any form permitting the sample to be heated in spot-heating manner, which sample is at the bent bottom portion 13 of the bent heating tube 3, it is preferable that the light source takes the form of an infrared lamp 18 the rays from which are easily transmitted through transparent glass, because the bent heating tube 3 is made of glass or quartz as already described above.

A focusing means for focusing the light issued from the light source on the bent bottom portion 13 of the bent heating tube 3 takes any form such as a lens system. However, it is preferable that the focusing means takes the form of a concave mirror 19 provided with a curved reflective surface one of the foci of which coincides in position with the steel sample in the bent bottom portion 13 of the bent heating tube 3, while the other of the foci of the curved reflective surface coincides in position with the infrared lamp 18, because the focusing operation of the concave mirror 19 is easy without any special focusing operation. By actuating the heat-ray spot-irradiating type heater 10, the sample in the bent bottom portion 13 of the bent heating tube 3 is heated to a temperature of 200° to 500° C. for a period of 10 to 100 seconds, preferably to a temperature of 350° C. for 90 seconds, so that the moisture adhered to the sample is evaporated. Consequently, in case the focus of the light source does not coincide in position with the steel sample, it is not possible to increase the accuracy of the hydrogen determined value in analysis due to an insufficient evaporation of the moisture adhered to the steel sample.

It is possible to employ any type of a hydrogen analyzing apparatus in connection with the preheating apparatus of the present invention, provided that such hydrogen analysis apparatus is provided with a fusion furnace in which the steel sample is fused so as to extract hydrogen. Among these analyzing apparatuses, a preferable one is an ordinary hydrogen analyzing apparatus according to an impulse furnace fusion-thermal conductivity method.

Figure 2:
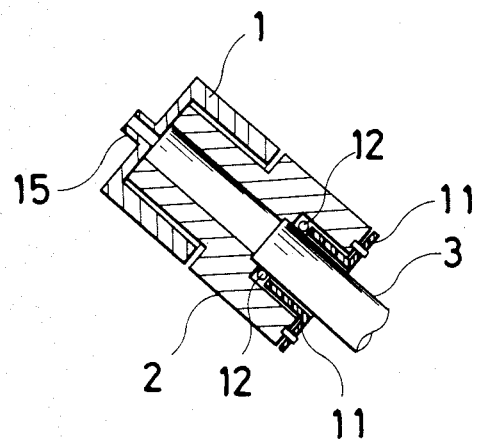
FIG. 2 is an enlarged sectional view of a sample inlet portion coupler employed in the preheating apparatus of the present invention, shown in FIG. 1.
Figure 3:
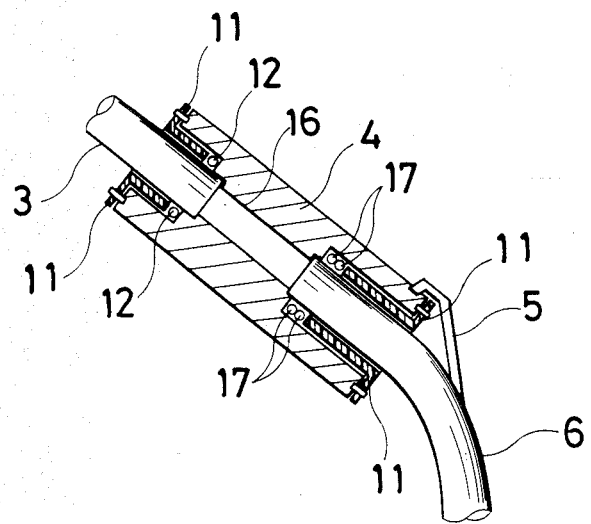
FIG. 3 is an enlarged sectional view of a lower coupler employed in the preheating apparatus of the present invention, shown in FIG. 1.

As shown in FIGS. 2 and 3, both the sample inlet portion coupler 2 and the lower portion coupler 4 are conventional couplers employed in the hydrogen microanalysis apparatus for analyzing gaseous hydrogen extracted from the steel sample, which couplers provide a sufficient gas tightness during rotary motion. Particularly, in the lower coupler 4, a pair of O-rings 17 are employed in a rotary section of the lower coupler 4 to provide a sufficient gas tightness.

The hydrogen analysis apparatus shown in FIG. 1 is provided with a carrier gas outlet 20 in a suitable portion of the stainless steel tube 6 thereof. The moisture evaporated from the steel sample heated by the use of the preheating apparatus of the present invention is extracted with the carrier gas, and then passed through a dessicant (not shown) so as to be absorbed thereby. A part of the hydrogen is also extracted from the steel sample during the preheating thereof in the preheating apparatus of the present invention, and then guided to a determination system of the hydrogen analysis apparatus after completion of absorption of moisture produced during the preheating of the steel sample, so that the determined value of that part of the hydrogen is obtained and added to the hydrogen determined value which is obtained by the ordinary fusion analysis method.

The hydrogen analysis apparatus is cut off from communication with the preheating apparatus of the present invention through a ball valve 7 during the preheating operation. After completion of the preheating operation, the ball valve 7 is opened so that the steel sample to be analyzed is transferred into a graphite crucible set in an impulse furnace of the hydrogen analysis apparatus (not shown), whereby hydrogen contained in the steel sample is determined.

Hydrogen contained in the steel sample is determined by the use of the preheating apparatus of the present invention as follows:

First, the sample inlet sealing plug 1 of the sample inlet coupler 2 is removed, and the steel sample is put into the preheating apparatus through the sample inlet portion coupler 2 and then the opening of the coupler 2 is closed with the sealing plug 1, whereby the steel sample is at the bent bottom portion 13 of the bent heating tube 3. At this time, the ball valve 7 is still closed, while empty-baking of the graphite crucible set in the impulse furnace of the hydrogen analysis apparatus is conducted to remove both moisture and gases adhered to the crucible.

Thereafter, the heat-ray spot-irradiating type heater 10 is actuated as the carrier gas is passed through the carrier gas inlet 15. On the other hand, infrared rays issued from the infrared lamp 18 are focused on the steel sample in the bent bottom portion 13 of the bent heating tube 3 by means of a concave mirror 19, so that the steel sample is heated to a temperature of 350° C. for about 90 seconds whereby the moisture adhered to the steel sample is evaporated to be discharged through the carrier gas outlet 20. At this time, since a part of the hydrogen contained in the steel sample is also extracted, such part of hydrogen is guided to the determination system of the hydrogen analysis apparatus by the use of the carrier gas so as to be determined.

Then, the heat-ray spot-irradiating type heater 10 is turned off and the ball valve 7 is closed, and the bent heating tube 3 is turned one-half turn in its circumferential direction whereby the steel sample falls from the bent heating tube 3 into the impulse furnace of the main body of the analysis apparatus through the ball valve 7 by gravity so as to enter the graphite crucible. Thereafter, the ball valve 7 is closed and the handle 9 is returned to its initial position to return the bent heating tube 3 to its initial position.

Then, according to the conventional operation, the steel sample is fused in the graphite crucible to extract hydrogen which is guided to the determination system of hydrogen and added to the hydrogen that was extracted during the preheating operation of the steel sample so as to be accurately determined in amount.

In addition, the preheating apparatus of the present invention is also applicable to the analysis of carbon contained in the steel sample. In this case, a high-frequency heating furnace is employed in place of the fusion furnace, so that the preheating temperature of 350° to 500° C. and a retention time of 20 to 120 seconds are realized for the steel sample to make it possible to precisely conduct the analysis of carbon contained in the steel sample as is in the analysis of hydrogen contained in the steel sample.

In the preheating apparatus of the present invention, since the steel sample in the transparent heating tube 3 is directly exclusively heated from outside by the use of the heat-ray spot-irradiating type heater 10 so that the moisture adhered to the steel sample is removed whereby hydrogen contained in the steel sample is analyzed, it is possible to decrease the time required for analysis while the analytical precision of hydrogen contained in the steel sample is improved, provided that the impulse furnace fusion-thermal conductivity method is employed in the analysis.

Further, in the analysis of carbon contained in the steel sample, such analysis of carbon is also conducted after removal of the carbon adhered to the steel sample, it is possible to decrease the time required for analysis while the analytical precision of carbon determination is improved, provided that a radio-frequency furnace combustion infrared ray absorption method is employed in the analysis.

In addition, since the heating tube of the present invention is separated from the heating apparatus, it is possible to easily transfer the steel sample into the fusion furnace after completion of the preheating of the steel sample, by simply rotating the bent heating tube 3 whereby retention and transfer of the steel sample is made easy and troubles regarding the sealing of the joint sections of the analytical apparatus are drastically reduced.

In the preheating apparatus of the present invention, since the heat-ray spot-irradiating type heater 10 is employed, it is possible to heat the steel sample in a spot-heating manner so that a water-cooling unit for the preheating apparatus is not required.

The preheating apparatus of the present invention is also applicable to: hydrogen analysis which is necessary to be conducted after removal of moisture adhered to a sample; and analysis of carbon according to a combustion method, in addition to the analysis of the steel sample, to make it possible to conduct a necessary analysis in practical use on-site/on-line accurately in a short time.

What is claimed is:

1. A preheating apparatus for removing moisture and carbon adhering to a solid sample before the sample is transferred into a furnace in which the sample is heated to extract hydrogen and carbon in gaseous forms for conducting an analysis of the thus-extracted hydrogen and carbon, comprising a tube including a bend adapted to receive and retain a solid sample placed in said tube when said bend is downwardly-directed and to discharge said sample from said tube when said bend is upwardly-directed;

means for rotating said tube about a longitudinal axis of said tube from a sample receiving and retaining position to a sample discharging position, infrared heating means, and means for focusing said infrared heating means on said tube so that when said tube is in said sample receiving and retaining position said infrared heating means is focused on said bend in said tube to heat said retained sample.

2. Apparatus as claimed in claim 1, further including means to sealingly connect a feed end of the tube to a source of inert gas and means to connect a discharge end of the tube to a furnace.

3. Apparatus as claimed in claim 1, in which said tube is of quartz or glass.

4. Apparatus as claimed in claim 1, said means for focusing said infrared heating means comprises mirror means.

* * * * *